(12) United States Patent
Aneja et al.

(10) Patent No.: US 12,256,897 B2
(45) Date of Patent: *Mar. 25, 2025

(54) BIOPSY CAP AND BIOPSY CAP HOUSING

(71) Applicant: BOSTON SCIENTIFIC MEDICAL DEVICE LIMITED, Galway (IE)

(72) Inventors: Harchetan S. Aneja, Amritsar (IN); Amit Bharos, Jabalpur (IN); Swami Upadhyay, Raipur (IN); Boopathi Rajarathnam, Salem (IN)

(73) Assignee: BOSTON SCIENTIFIC MEDICAL DEVICE LIMITED, Galway (IE)

( * ) Notice: Subject to any disclaimer, the term of this patent is extended or adjusted under 35 U.S.C. 154(b) by 0 days.

This patent is subject to a terminal disclaimer.

(21) Appl. No.: 18/200,362

(22) Filed: May 22, 2023

(65) Prior Publication Data

US 2023/0284881 A1 Sep. 14, 2023

Related U.S. Application Data

(63) Continuation of application No. 16/671,889, filed on Nov. 1, 2019, now Pat. No. 11,690,499.

(Continued)

(51) Int. Cl.
*A61B 1/00* (2006.01)
*A61B 1/015* (2006.01)
(Continued)

(52) U.S. Cl.
CPC ...... *A61B 1/00137* (2013.01); *A61B 1/00064* (2013.01); *A61B 1/0011* (2013.01);
(Continued)

(58) Field of Classification Search
CPC .......................... A61B 1/00137; A61B 1/0014
See application file for complete search history.

(56) References Cited

U.S. PATENT DOCUMENTS

| 4,198,959 A | 4/1980 | Otani |
| 5,312,363 A | 5/1994 | Ryan et al. |

(Continued)

FOREIGN PATENT DOCUMENTS

| AU | 279199 A1 | 2/2000 |
| AU | 5698701 A | 11/2001 |

(Continued)

OTHER PUBLICATIONS

International Search Report and Written Opinion for the International Patent Application No. PCT/IB2019/059413, dated Feb. 17, 2020, 10 pages.

(Continued)

*Primary Examiner* — Timothy J Neal
(74) *Attorney, Agent, or Firm* — Seager, Tufte & Wickhem, LLP

(57) ABSTRACT

The present disclosure relates generally to the field of medical instruments. In particular, the present disclosure relates to a biopsy cap and endoscope biopsy cap housing with improved stability and stress distribution to securely and removably attach to an endoscope biopsy port. In one example, a biopsy cap housing may include a first center-split half comprising a first half of an upper and lower chamber and first pivot member, and a second center-split half comprising a second half of an upper and lower chamber, and second pivot member, wherein mating surfaces of the first and second center-split halves may be configured to interlock to define the upper and lower chambers.

20 Claims, 7 Drawing Sheets

Related U.S. Application Data

(60) Provisional application No. 62/834,201, filed on Apr. 15, 2019, provisional application No. 62/834,192, filed on Apr. 15, 2019, provisional application No. 62/768,808, filed on Nov. 16, 2018, provisional application No. 62/755,024, filed on Nov. 2, 2018.

(51) Int. Cl.
  *A61B 1/018* (2006.01)
  *A61B 10/02* (2006.01)
  *A61B 10/04* (2006.01)
  *B29D 99/00* (2010.01)

(52) U.S. Cl.
  CPC ........ *A61B 1/0014* (2013.01); *A61B 1/00147* (2013.01); *A61B 1/015* (2013.01); *A61B 1/018* (2013.01); *A61B 10/0275* (2013.01); *A61B 10/04* (2013.01); *B29D 99/0053* (2013.01)

(56) References Cited

U.S. PATENT DOCUMENTS

| | | |
|---|---|---|
| 5,743,884 A | 4/1998 | Hasson et al. |
| 6,254,529 B1 | 7/2001 | Ouchi |
| 6,605,075 B1 | 8/2003 | Burdulis |
| 6,606,515 B1 | 8/2003 | Windheuser et al. |
| 7,226,411 B2 | 6/2007 | Akiba |
| 7,473,221 B2 | 1/2009 | Ewers et al. |
| 7,637,863 B2 | 12/2009 | Deal et al. |
| 7,670,285 B2 | 3/2010 | Yamaya |
| 7,670,316 B2 | 3/2010 | Windheuser et al. |
| 7,803,107 B2 | 9/2010 | Carrillo |
| 7,967,744 B2 | 6/2011 | Kaye et al. |
| 8,012,129 B2 | 9/2011 | Bettuchi et al. |
| 8,152,774 B2 | 4/2012 | Pasqualucci |
| 8,231,525 B2 | 7/2012 | Cohen et al. |
| 8,333,693 B2 | 12/2012 | Hamazaki |
| 8,343,041 B2 | 1/2013 | Byers et al. |
| 8,434,041 B2 | 4/2013 | Chen et al. |
| 8,480,570 B2 | 7/2013 | Tinkham et al. |
| 8,702,596 B2 | 4/2014 | Kaye et al. |
| 8,753,264 B2 | 6/2014 | Carrillo, Jr. et al. |
| 8,974,377 B2 | 3/2015 | Yamane |
| 9,089,261 B2 | 7/2015 | Greenburg et al. |
| 9,101,738 B2 | 8/2015 | Eden |
| 9,149,173 B2 | 10/2015 | Scopton et al. |
| 9,622,776 B2 | 4/2017 | Oberlaender et al. |
| 9,955,998 B2 | 5/2018 | Kleyman |
| 9,986,895 B2 | 6/2018 | Meloul |
| 11,064,870 B2 | 7/2021 | Rajarathnam et al. |
| 2005/0090835 A1 | 4/2005 | Deal et al. |
| 2005/0171402 A1 | 8/2005 | Cohen et al. |
| 2006/0195117 A1 | 8/2006 | Rucker et al. |
| 2007/0238928 A1 | 10/2007 | Maseda et al. |
| 2007/0244356 A1 | 10/2007 | Carillo, Jr. et al. |
| 2007/0282166 A1 | 12/2007 | Ayala et al. |
| 2007/0293719 A1 | 12/2007 | Scopton et al. |
| 2009/0005799 A1 | 1/2009 | Franer et al. |
| 2009/0088600 A1 | 4/2009 | Meloul |
| 2009/0287052 A1 | 11/2009 | Amos et al. |
| 2010/0081878 A1 | 4/2010 | Byers et al. |
| 2010/0087705 A1 | 4/2010 | Byers et al. |
| 2010/0087710 A1 | 4/2010 | Weldon et al. |
| 2010/0240956 A1 | 9/2010 | Secrest et al. |
| 2012/0004507 A1 | 1/2012 | Kaye |
| 2012/0071713 A1 | 3/2012 | Kaye et al. |
| 2012/0253128 A1 | 10/2012 | Yamane |
| 2013/0150793 A1 | 6/2013 | Beissel et al. |
| 2013/0304116 A1 | 11/2013 | Yamane |
| 2015/0190170 A1 | 7/2015 | Frederick et al. |
| 2016/0206859 A1 | 7/2016 | Eden |
| 2017/0202438 A1 | 7/2017 | Ogi |
| 2017/0319828 A1 | 11/2017 | Doepker et al. |
| 2018/0310806 A1 | 11/2018 | Gavalis et al. |
| 2019/0046016 A1 | 2/2019 | Rajarathnam et al. |
| 2019/0142463 A1 | 5/2019 | Zhu |
| 2020/0138272 A1 | 5/2020 | Neelamegam et al. |
| 2020/0138273 A1 | 5/2020 | Neelamegam et al. |
| 2020/0138274 A1 | 5/2020 | Aneja et al. |
| 2020/0138276 A1 | 5/2020 | Aneja et al. |
| 2020/0138277 A1 | 5/2020 | Neelamegam et al. |
| 2020/0138419 A1 | 5/2020 | Aneja et al. |

FOREIGN PATENT DOCUMENTS

| | | |
|---|---|---|
| CN | 105816208 A | 8/2016 |
| CN | 205697867 U | 11/2016 |
| EP | 1997444 A2 | 12/2008 |
| EP | 1406691 B1 | 1/2010 |
| EP | 2505119 A1 | 10/2012 |
| EP | 2564758 A1 | 3/2013 |
| EP | 2574271 A1 | 4/2013 |
| EP | 2574271 B1 | 11/2014 |
| EP | 2020901 B1 | 7/2016 |
| JP | S6129703 A | 2/1986 |
| JP | H11253396 A | 9/1999 |
| JP | 2003533297 A | 11/2003 |
| JP | 2005080867 A | 3/2005 |
| JP | 2008123063 A | 5/2008 |
| JP | 2009268777 A | 11/2009 |
| JP | 2001104315 A | 4/2011 |
| WO | 9959664 A1 | 11/1999 |
| WO | 0187398 A2 | 11/2001 |
| WO | 2005011791 A2 | 2/2005 |
| WO | 2008101286 A1 | 8/2008 |
| WO | 2009143129 A1 | 11/2009 |
| WO | 2009143137 A1 | 11/2009 |
| WO | 2018024109 A1 | 2/2018 |

OTHER PUBLICATIONS

International Search Report and Written Opinion for the International Patent Application No. PCT/IB2019/059404, dated Feb. 17, 2020, 10 pages.

International Search Report and Written Opinion for the International Patent Application No. PCT/IB2019/059407, dated Feb. 14, 2020, 11 pages.

International Search Report and Written Opinion for the International Patent Application No. PCT/IB2019/059408, dated Feb. 14, 2020, 12 pages.

International Search Report and Written Opinion for the International Patent Application No. PCT/IB2019/059409, dated Feb. 13, 2020, 11 pages.

Cook Medical—"Fusion® Wire Guide Locking Device" URL: https://www.cookmedical.com/products/esc_fswl_webds/ © Cook 2021.

International Search Report and Written Opinion for the International Patent Application No. PCT/IB2019/059411, dated Jun. 25, 2020, 14 pages.

BIOPSY CAP AND BIOPSY CAP HOUSING

CROSS-REFERENCE TO RELATED APPLICATIONS

This application is a continuation of and claims the benefit of the earlier filing date of U.S. patent application Ser. No. 16/671,889, filed on Nov. 1, 2019, which claims the benefit of priority under 35 USC § 119 to U.S. Provisional Patent Application Ser. No. 62/755,024, filed Nov. 2, 2018, and titled "Attachments for Endoscopes"; U.S. Provisional Patent Application Ser. No. 62/768,808, filed Nov. 16, 2018, and titled "Internal Seal for Biopsy Cap"; U.S. Provisional Patent Application Ser. No. 62/834,192, filed Apr. 15, 2019, and titled "Biopsy Cap and Biopsy Cap Housing"; and to U.S. Provisional Patent Application Ser. No. 62/834,201, filed Apr. 15, 2019, and titled "Devices, Systems, and Methods For Providing Sealable Access To A Working Channel," the disclosures of which applications are each incorporated by reference herein in their entireties and for all purposes.

FIELD

The present disclosure relates generally to the field of medical instruments. More particularly, the present disclosure pertains to medical instruments for use with an endoscope, such as a biopsy cap and a biopsy cap housing with improved stability and stress distribution, for example, to securely attach to an endoscope biopsy port.

BACKGROUND

Conventional endoscope biopsy cap housings and biopsy caps can include a variety of deficiencies which may contribute—both individually and cumulatively—to component breakage, unnecessarily complicated or additional procedural steps and/or prolonged procedure times. For example, conventional biopsy cap housings tend to permit axial and rotational movement of the housing and/or cap during device exchange. In addition, exchange of larger diameter medical instruments (e.g., catheters, stent introducers, etc.) through the biopsy cap tends to exert a radially outward force which may cause the two center-split halves of conventional biopsy cap housings to partially or completely separate/disengage from each other. Adhesives applied to the center-split halves may minimize such separation but result in increased assembly time and cost. Locking or unlocking a guidewire to the hook(s) located on one side of a conventional biopsy cap housing tends to exert a radially outward force on one of the center-split halves, which may cause the center-split halves to move in opposite directions and partially or completely separate/disengage from each other. Excessive flexing due to lateral forces applied to one or both center-split halves, e.g., during disengagement of the biopsy cap housing from the biopsy port, may concentrate stress on the locks which secure the biopsy cap housing to the endoscope port, resulting in a fracture of one or more of the locks. Any fracturing of components or separation between the center-split halves resulting from these forces may result in compromised stability between the biopsy cap housing and the endoscope biopsy port. In addition, the cumulative effects of these separation forces may decrease the operational longevity of the biopsy cap housing.

A variety of advantageous medical outcomes may therefore be realized by the biopsy cap and biopsy cap housing embodiments of the present disclosure.

SUMMARY

In one aspect, the present disclosure relates to a biopsy cap housing comprising a first center-split half and a second center-split half. The first center-split half may include a first portion defining a first half of an upper chamber and a second portion defining a first half of a lower chamber. A first pivot member may be integrally formed with the first portion of the first center-split half. A first slit may extend through a sidewall of the first and second portions of the first center-split half and in substantial alignment with the first pivot member. The second center-split half may include a first portion defining a second half of the upper chamber and a second portion defining a second half the lower chamber. A second pivot member may be integrally formed with the first portion of the second center-split half. A second slit may extend through a sidewall of the first and second portions of the second center-split half and in substantial alignment with the second pivot member. Mating surfaces of the first and second center-split halves may be configured to interlock to define the upper and lower chambers.

In the described and other embodiments within the scope of the present disclosure, an elevated surface of the first pivot member may extend into the upper chamber and an elevated surface of the second pivot member may extend into the upper chamber substantially opposite the first pivot member. The upper chamber may be configured to receive a biopsy cap. The lower chamber may be configured to receive an endoscope biopsy port. The first and second pivot members may include a thickness greater than a wall thickness of the first and second center-split halves. A force applied to the first portions of the first and second center-split halves may move the second portions of the first and second center-split halves away from each other. A force applied to the second portions of the first and second center-split halves may move the first portions of the first and second center-split halves away from each other. The elevated surfaces of the first and second pivot members may be configured to engage a corresponding recessed portion formed within an outer wall of a biopsy cap disposed within the upper chamber. A first locking hook may be attached to a proximal end of the first center-split half and a second locking hook may attached to a proximal end of the second center-split half. The first and second locking hooks may be substantially adjacent to each other when the first and second center-split halves are interlocked. An inner surface of the first portions of the first and second center-split halves may include a surface feature configured to engage a corresponding surface feature formed on or within an outer wall of a biopsy cap disposed within the upper chamber. The surface feature of the housing may include a lip extending into a proximal end of the upper chamber. The surface feature of the biopsy cap may include a wedge extending inward from a top surface of the biopsy cap. The lip may be configured to engage the top surface of the wedge of the biopsy cap. The surface feature of the housing may include a wedge formed within the inner surfaces of the first and second portions of the first and second center-split halves. The surface feature of the biopsy cap may include a wedge extending outward from an outer wall of the biopsy cap top. The wedge of the housing may be configured to engage the wedge of the biopsy cap. The mating surface of the first center-split half may include one or more projections and the mating surface of the second center-split half may include one or more receiving elements. The projections may be configured to be received within corresponding receiving elements. The one or more projections may include one or more pins and the one or more receiving elements may include one or more pin holes. The one or more pins and corresponding one or more pin holes may be located at a proximal end of the first portions of the first and second center-split halves. The one or more pins and corresponding one or more pin holes may be located at a proximal end of the second portions of the first and second center-split halves. The one or more projections may include one or more pegs and the one or more receiving elements may include one or more sockets. The one or more pegs and corresponding one or more sockets may be located at a proximal end of the second portions of the first and second center-split halves. The one or more projections may include one or more snap-locks and the one or more receiving elements may include one or more snap-lock receivers. The one or more snap-locks and corresponding one or more snap-lock receivers may be located at a proximal end of the first portions of the first and second center-split halves. The one or more snap-locks and corresponding one or more snap-lock receivers may be located at a proximal end of the second portions of the first and second center-split halves. The one or more snap-locks may include an angled surface configured to positively engage a corresponding angled surface of the one or more snap-lock receivers. An inner surface of the second portions of the first and second center-split halves may include one or more locking members extending into the lower chamber and configured to releasably engage an outer surface of an endoscope biopsy port disposed within the lower chamber. An inner surface of the second portions of the first and second center-split halves may include one or more platforms extending into the lower chamber on opposite sides of the first and second slits and between the one or more locking members. An end of the one or more locking members and a surface of the one or more platforms may be separated by a distance within the lower chamber when a force is not applied to the first portions of the first and second center-split halves. An end of the one or more locking members and a surface of the one or more platforms may be in contact when a force is applied to the first portions of the first and second center-split halves. The force applied to the first portions of the first and second center-split halves may be an inward compressive force configured to move the second portions of the first and second center-split halves away from each other. The contact between the one or more locking members and the surface of the one or more platforms may prevent at least one of the locking members from breaking due to over-extension.

In one aspect, the present disclosure relates to a biopsy cap comprising one or more surface features formed on or within the biopsy cap. The one or more surface features may be configured to frictionally and/or compressingly engage a corresponding surface feature formed on or within an inner surface of a first portion of first and second center-split halves of a biopsy cap housing. The biopsy cap may include a first surface feature attached to or integrally formed with a proximal end of the biopsy cap and second and third surface features attached to or integrally formed with an outer wall of the biopsy cap. The one or more surface features may include first and second recessed portions integrally formed within an outer wall of the biopsy cap and separated from the second and third surface features by approximately 90-degrees relative to an outer circumference of the biopsy cap. The biopsy cap may be formed from or otherwise include a variety of compressible materials (e.g., silicone, rubbers, etc.) formed as a single unitary structure using. The surface feature may include a substantially contiguous lip. The surface feature may include substantially contiguous wedges. The surface feature may include recessed portions.

In one aspect, the present disclosure relates to a biopsy cap assembly comprising a first center-split housing half and a second center-split housing half. The first center-split half may include a first portion defining a first half of an upper chamber and a second portion defining a first half of a lower chamber. A first pivot member may be integrally formed with the first portion of the first center-split half. The second center-split half may include a first portion defining a second half of the upper chamber and a second portion defining a second half the lower chamber. A second pivot member may be integrally formed with the first portion of the second center-split half. Mating surfaces of the first and second center-split housing halves may be configured to interlock to define the upper and lower chambers. A biopsy cap may be disposed within the upper chamber.

In the described and other embodiments within the scope of the present disclosure, an outer wall of the biopsy cap may include recessed portions formed therein. An elevated surface of the first pivot member may extend into the upper chamber and an elevated surface of the second pivot member may extend into the upper chamber substantially opposite the first pivot member. The elevated surfaces may frictionally engage the recessed portions of the biopsy cap. The first and second pivot members may include a thickness greater than a wall thickness of the first and second center-split housing halves. The housing may include a lip extending into a proximal end of the upper chamber and the biopsy cap may include a wedge extending outward from a top surface of the cap. The lip may be configured to engage the top surface of the wedge. The housing may include a wedge formed within the inner surfaces of the first and second portions of the first and second center-split housing halves. The biopsy cap may include a wedge extending outward from an outer wall of the biopsy cap top. The wedge of the housing may be configured to engage the wedge of the biopsy cap.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures.

DETAILED DESCRIPTION

Figure 1A:
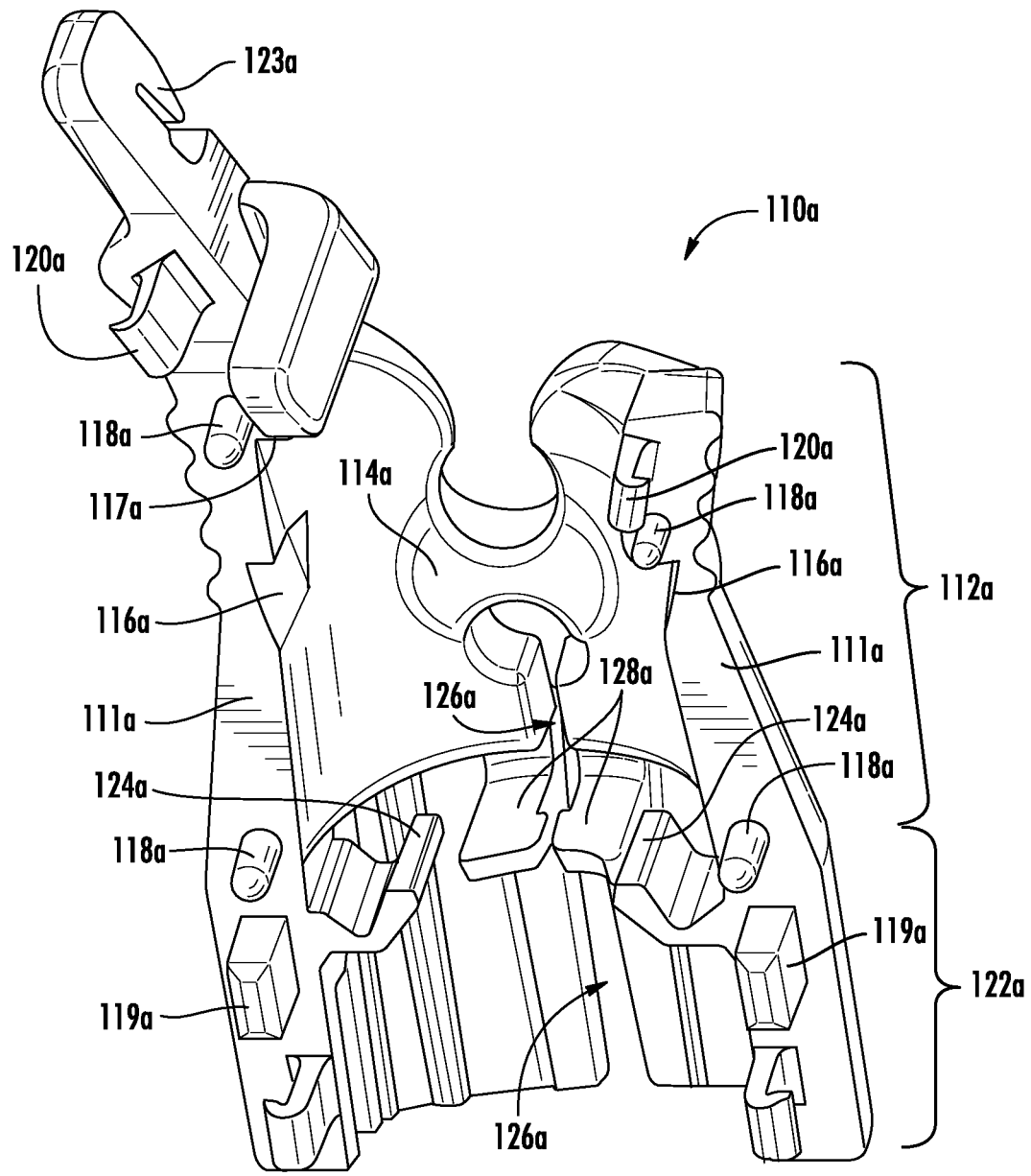
FIGS. 1A-1C provide perspective views of center-split halves of a biopsy cap housing, according to one embodiment of the present disclosure.

The present disclosure is not limited to the particular embodiments described herein. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

Although embodiments of the present disclosure are described with specific reference to biopsy caps and biopsy cap housings configured to allow the delivery and/or exchange of a variety of medical instruments through the biopsy cap and port of an endoscope, laparoscope, or other visualization systems such as the Spy Glass™ Direct Visualization System (Boston Scientific Corp., Marlborough, MA), it should be appreciated that such designs may be adapted to fit and/or be used with a variety of medical instruments and medical applications which include sealable access.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

As used herein, the term "distal" refers to the end farthest away from the medical professional when introducing a device into a patient, while the term "proximal" refers to the end closest to the medical professional when introducing a device into a patient.

In various embodiments, features and advantages of providing sealable access to a working channel, e.g., of an endoscope, may be realized in combination with a biopsy cap and biopsy cap housing. Such sealable access to a working channel, which may be reinforced, may be implemented with features throughout the disclosures of U.S. patent application Ser. No. 16/100,960, filed Aug. 10, 2018, and titled "Biopsy Cap For Use With Endoscope"; United States Patent Application Publication No. 2020/0138274, filed on Nov. 1, 2019, and titled "Attachments For Endoscopes"; United States Patent Application Publication No, 2020/0138272, filed on Nov. 1, 2019, and titled "Devices, Systems, And Methods For A Biopsy Cap And Housing"; United States Patent Application Publication No. 2020/0138277, filed on Nov. 1, 2019, and titled, "Devices, Systems, And Methods For Providing Sealable Access To A Working Channel"; United States Patent Application Publication No. 2020/0138273, filed on Nov. 1, 2019, and titled "Internal Seal for Biopsy Cap"; United States Patent Application Publication No. 2020/0138276, filed on Nov. 1, 2019, and titled "Devices, Systems, and Methods for Providing Sealable Access to a Working Channel", which applications are each hereby incorporated by reference herein in their entirety and for all purposes.

Figure 1B:
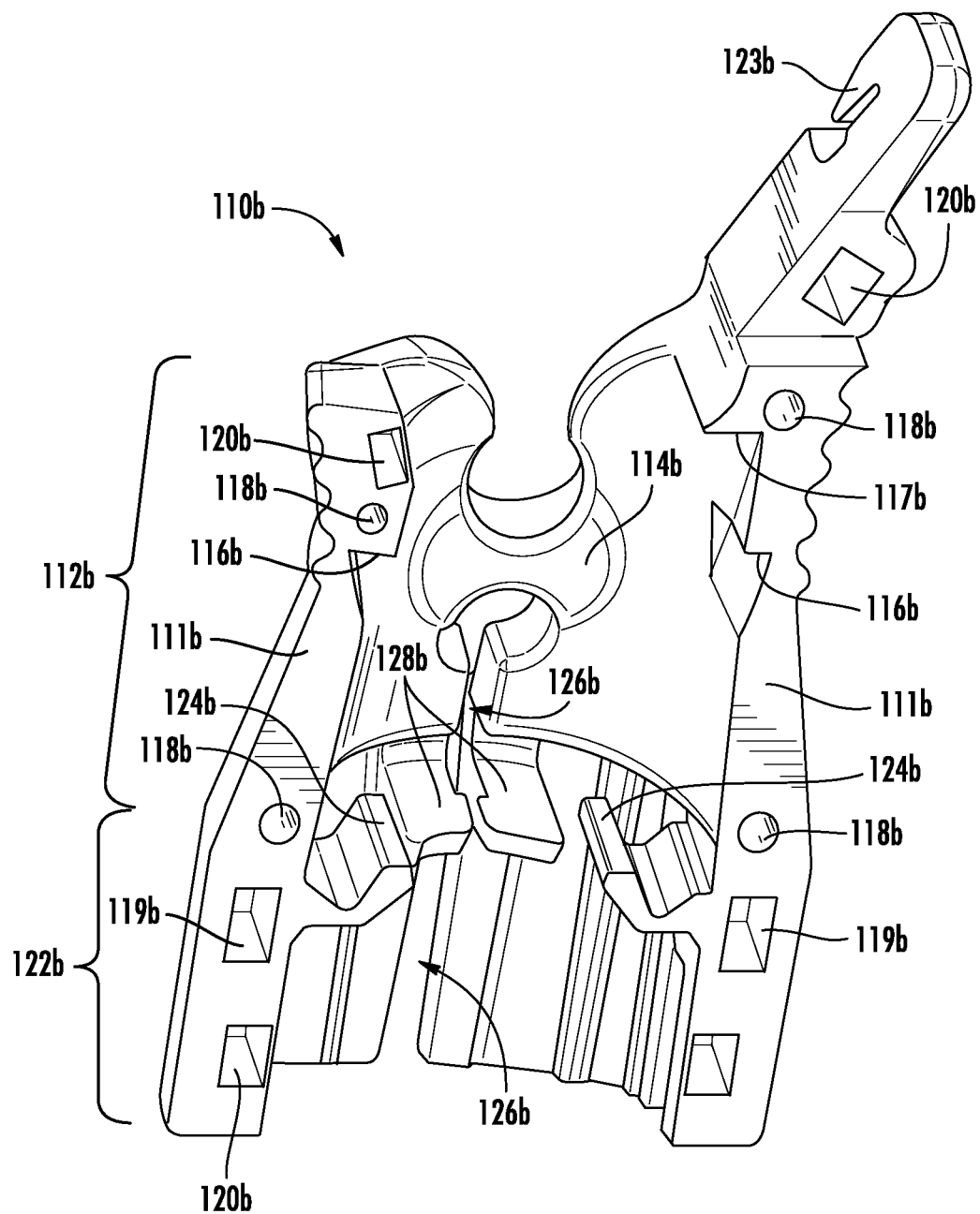
Figure 4A:
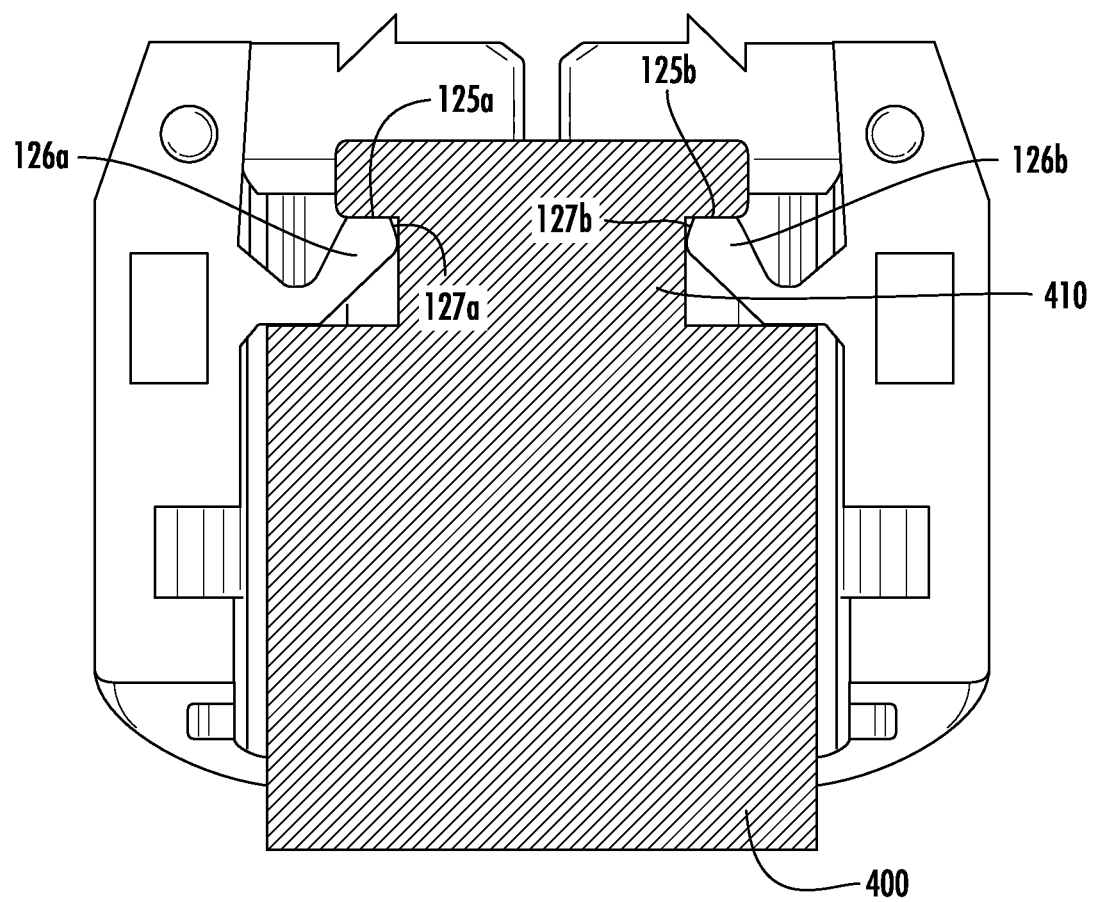
FIGS. 4A-4C provide perspective views of V-locks of a biopsy cap housing, according to one embodiment of the present disclosure.

Referring to FIGS. 1A-1B, in an embodiment of a biopsy cap housing of the present disclosure may include first and second center-split halves 110a, 110b (e.g., first and second housing portions or pieces) configured to mate or interlock with each other to define a first portion 112a, 112b, (e.g., an upper chamber, first chamber, top chamber, etc.) configured to securely receive a biopsy cap 300 (e.g. in FIG. 2) and a second portion 122a, 122b, (e.g., a lower chamber, second chamber, bottom chamber, etc.) configured to securely and reversibly engage the neck 610 of an endoscope biopsy port 400 (FIG. 4A).

Figure 2:
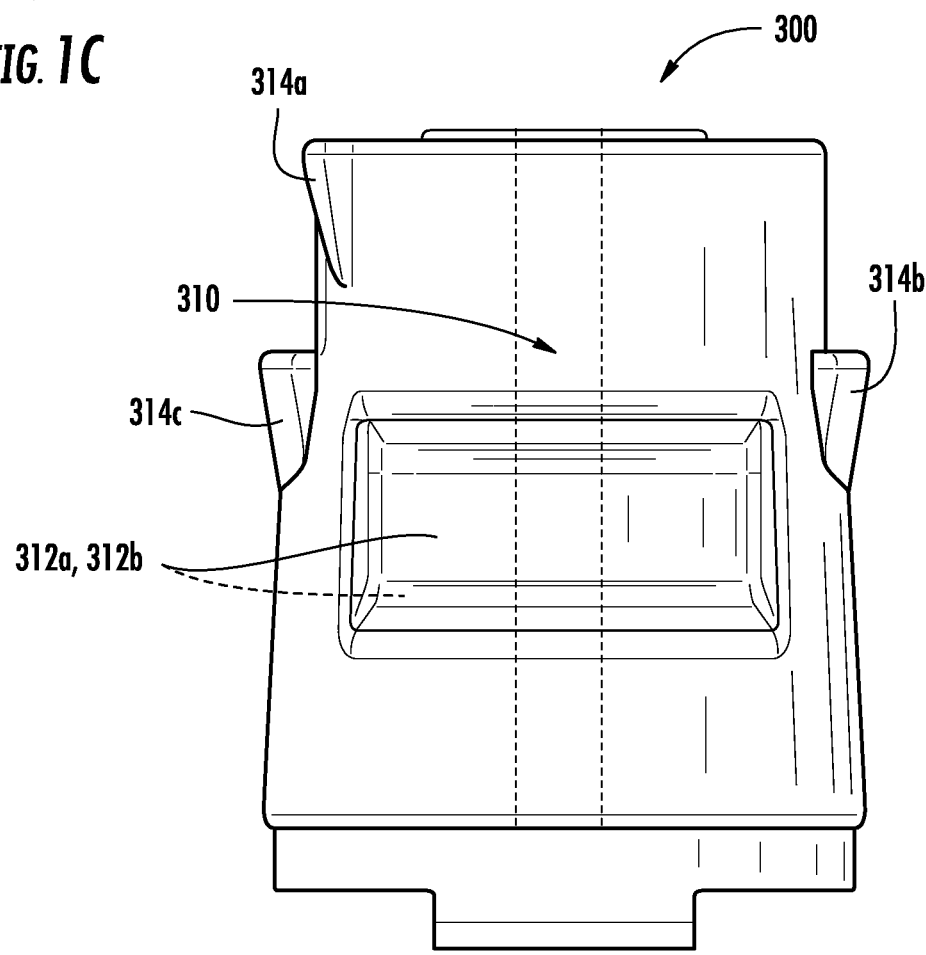
FIG. 2 provides a perspective view of a biopsy cap, according to one embodiment of the present disclosure.

Referring to FIG. 1A, in an embodiment, a first center-split half 110a (e.g., first side, lock side, etc.) of the biopsy cap housing 100 may include a first (e.g., top, upper) portion 112a defining a first half (e.g., a substantially hemi-cylindrical half) of the upper chamber, and a second (e.g., bottom, lower) portion 122a defining a first half (e.g., a substantially hemi-cylindrical half) of the lower chamber. A first locking hook 123a (e.g., guidewire locking hook) and a guide are 130 may be attached to or integrally formed with a proximal end of the first portion 112a. A first pivot member 114a (e.g., first pivot button, first pivot feature, etc.) may be integrally formed with an approximate midpoint of the first portion 112a, and a first slit 126a (e.g., opening, slot, etc.) may extend through a sidewall of the first and second portions 112a, 122a and in substantial alignment with (e.g., on the same side as, directly below, etc.) the first pivot member 114a. The first pivot member 114a may include a substantially radially raised or elevated surface (e.g., enlarged portion, projection, etc.) extending into the first half of the upper chamber, e.g., to engage a corresponding recessed portion 312a formed within an outer wall of a biopsy cap 300 (FIG. 2).

In an embodiment, an inner surface of the first portion 112a of the first center-split half 110a may include a surface feature(s) configured to compressingly and/or frictionally engage a corresponding surface feature of a biopsy cap. In some embodiments, the surface feature(s) may include a lip 117a (e.g., step feature, etc.) integrally formed with an inner wall of the first center-split half 110a and extending into the first half of the upper chamber at or near a proximal end of the first portion 112a. In various embodiments, the surface feature(s) may include a pair of wedges 116a (e.g., indentations, recessed portions, etc.) formed within the inner wall of the first portion 112a distal to the lip 117a and on opposite sides (e.g., separated by approximately 180 degrees) of the first half of the first portion 112a.

In an embodiment, one or more locking members 124a (e.g., V-locks, etc.) may be attached to or integrally formed with an inner wall of the first center-split half 110a at or near a proximal end of the second portion 122a and on opposite sides (e.g., separated by approximately 180 degrees) of the first half of the second portion 122a. The locking member(s) 124a may be configured to releasably engage a biopsy port 400 (e.g., at neck 410) disposed within the second portion 122a (FIG. 4A). For example, an end of the locking member(s) 124a may include a pair of substantially perpendicular surfaces 125a, 127a configured to engage (e.g., contact, fit within, etc.) a substantially 90-degree surface (e.g., a bottom or lower surface of a lip) of the neck 410 of the biopsy port 400. In addition, one or more platforms (e.g., stops, etc.) may be attached to or integrally formed with an inner wall of the first center-split half 110a on opposite sides of the first slit 126a and between the locking member(s) 124a.

In an embodiment, one or more projections may be attached to or integrally formed with a mating surface 111a of the first and second portions 112a, 122a of the first center-split half 110a. In various embodiments, the projection(s) may include one or more pins 118a (e.g., posts, rods, etc.) with a substantially spherical or cylindrical outer dimension. In various additional embodiments, the projections(s) may include one or more pegs 119a (e.g., blocks, etc.) with a substantially square or rectangular outer dimension. In various additional embodiments, the projections(s) may include one or more snap-locks 120a (e.g., arms, etc.) with a substantially curved or hooked end.

By way of non-limiting example, in an embodiment, two pins 118a may extend from the mating surface 111a at or near a proximal end of the first portion 112a and two pins 118a may extend from the mating surface 111a adjacent to the locking member(s) 124a. Two snap-locks 120a may extend from the mating surface 111a at or near the proximal end of the first portion 112a and proximal to the pins 118a and two snap-locks may extend from the mating surface 111a at or near a distal end of the second portion 122a. Two pegs 119a may extend from the mating surface 111a adjacent to the locking member(s) 124a, distal to the pins 118a and proximal to the pegs 119a.

Referring to FIG. 1B, in an embodiment, a second center-split half 110b (e.g., second side, groove side, etc.) of the biopsy cap housing 20 may include a first (e.g., top) portion 112b defining a second half (e.g., a substantially hemi-cylindrical half) of the upper chamber, and a second (e.g., bottom) portion 122b defining a second half (e.g., a substantially hemi-cylindrical half) of the lower chamber. A second locking hook 123b (e.g., guidewire locking hook) may be attached to or integrally formed with a proximal end of the first portion 112b. A second pivot member 114b (e.g., second pivot button, second pivot feature, etc.) may be integrally formed with an approximate midpoint of the first portion 112b, and a second slit 126b (e.g., opening, etc.) may extend through a sidewall of the first and second portions 112b, 122b and in substantial alignment with (e.g., one the same side as, directly below, etc.) the second pivot member 114b. The second pivot member 114b may include a raised or elevated surface (e.g., enlarged portion, etc.) extending into the first half of the upper chamber, e.g., to engage a corresponding recessed portion 312b (e.g., groove, indentation, etc.) formed within an outer wall of a biopsy cap 300 (FIG. 2).

In one embodiment, an inner surface of the first portion 112b of the second center-split half 110b may include a surface feature(s) configured to compressingly and/or frictionally engage a corresponding surface feature of the biopsy cap. In one embodiment, the surface feature(s) may include a lip 117b (e.g., step feature, etc.) integrally formed with an inner wall of the second center-split half 110b and extending into the first half of the upper chamber at or near a proximal end of the first portion 112b. In one embodiment, the surface feature(s) may include a pair of wedges 116b (e.g., indentation, recessed portion, etc.) formed within the inner wall of the second portion 112b distal to the lip 117b and on opposite sides (e.g., separated by approximately 180 degrees) of the first half of the upper chamber.

In one embodiment, one or more locking members 124b (e.g., V-locks, etc.) may be attached to or integrally formed with an inner wall of the second center-split half 110b at or near a proximal end of the second portion 122b and on opposite sides (e.g., separated by approximately 180 degrees) of the second half of the lower chamber. The locking member(s) 124b may be configured to releasably engage the neck 410 of a biopsy port 400 disposed within the lower chamber (FIG. 4A). For example, an end of the locking member(s) 124b may include a pair of substantially perpendicular surfaces 125b, 127b configured to engage (e.g., contact, fit within, etc.) a substantially 90-degree surface (e.g., a bottom or lower surface of a lip) of the neck 410 of the biopsy port 400. In addition, one or more platforms 128b (e.g., stops, etc.) may be attached to or integrally formed with an inner wall of the second center-split half 110b on opposite sides of the second slit 126b and between the locking member(s) 124b.

Figure 1C:
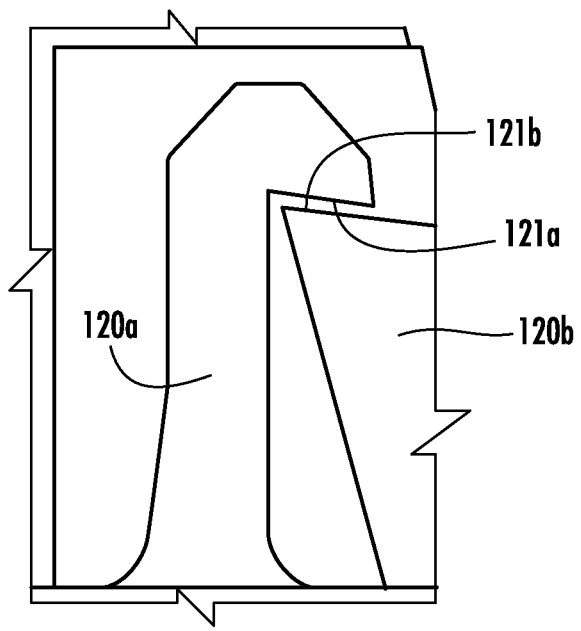

In one embodiment, one or more receiving elements (e.g., receiving features, etc.) may be integrally formed within a mating surface 111b of the first and second portions 112b, 122b of the second center-split half 110b and configured to receive/engage the corresponding one or more projection(s) of the first center-split half 110a in a friction or interference fit, e.g., such that the first and second center-split halves 110a, 110b may interlock in a snap-fit configuration to form an assembled biopsy cap housing 110. In various embodiments, the receiving element(s) may include one or more pin holes 118b (e.g., posts, rods, etc.) with a substantially spherical or cylindrical inner dimension configured to frictionally receive the corresponding substantially spherical or cylindrical outer dimension of the respective pin(s) 118a. In various additional embodiments, the receiving element(s) may include one or more sockets 119b with a substantially square or rectangular inner dimension configured to frictionally receive the corresponding substantially square or rectangular outer dimension of the respective peg(s) 119a. In various additional embodiments, the receiving element(s) may include one or more snap-lock receivers 120b with a substantially curved or hooked inner dimension configured to receive the corresponding substantially curved or hooked end of the snap-lock(s) 120a. Referring to FIG. 1C, in one embodiment, the one or more snap-locks 120a of the present disclosure may include a recessed angled surface 121a configured to frictionally and/or compressingly contact/engage a corresponding angled surface 121b of the respective or more snap-lock receivers 120b. In various embodiments, the interface between these opposing angled surfaces may provide a "positive locking" interaction with a greater locking force/interaction than between corresponding non-angled surfaces.

By way of non-limiting example, in one embodiment, two pin holes 118b may be formed within the mating surface 111b at or near a proximal end of the first portion 112b and two pin holes 118b may be formed within the mating surface 111b adjacent to the locking member(s) 124b. Two snap-lock receivers 120b may be formed within the mating surface 111b at or near the proximal end of the first portion 112b and proximal to the pin holes 118b and two snap-lock receiver 120bs may be formed within the mating surface 111b at or near a distal end of the second portion 122b. Two sockets 119b may be formed within the mating surface 111b adjacent to the locking member(s) 124b, distal to the pin holes 118b and proximal to the snap-lock receivers 120b.

In one embodiment, a biopsy cap housing 100 of the present disclosure may be assembled by aligning the mating surfaces 111a, 111b of the first and second center-split halves 110a, 110b such that each of the one or more projections (e.g., pin(s) 118a, peg(s) 119a and snap-lock(s) 120a) is aligned with the corresponding one or more receiving elements (e.g., pin hole(s) 118b, socket(s) 119b and snap-lock receiver(s) 120b) and then compressing or squeezing the first and second center-split halves 110a, 110b together in a snap-fit configuration. In various embodiments, the first and second locking hooks 123a, 123b may be substantially adjacent to each other when the biopsy cap housing 100 is assembled and configured to securely engage a proximal portion of a guidewire. In addition, the respective surface features of the first portions 112a, 112b of the first and second center-split halves 110a, 110b may substantially aligned to provide contiguous surface features to prevent or limit axial and/or rotational movement of a biopsy cap 300 disposed within the upper chamber and/or to prevent fluid flow (e.g., leakage) around an outer surface of the biopsy cap 300. For example, the lips 117a, 117b of the first and second portions 112a, 112b may align to form a substantially contiguous lip extending into the upper chamber at or near a proximal end of the biopsy cap housing 100 and the wedges 116a, 116b may substantially align to form contiguous wedges on opposites sides of the upper chamber.

Referring to FIG. 2, in one embodiment, a biopsy cap 300 of the present disclosure may include a surface feature(s) formed on or within the biopsy cap and configured to frictionally and/or compressingly engage a corresponding surface feature formed on or within an inner surface of the first portions of the first and second center-split halves 110a, 110b. In one embodiment, the biopsy cap 300 may include a first surface feature 314a attached to or integrally formed with a proximal end (e.g., top surface) of the biopsy cap 300 and second and third surface features 314b, 314c attached to or integrally formed with an outer wall of the biopsy cap 300. In addition, or alternatively, the surface feature(s) may include first and second recessed portions 312a, 312b integrally formed within an outer wall of the biopsy cap 300 and separated from the second and third surface features 314b, 314c by approximately 90-degrees relative to an outer circumference of the biopsy cap 300. In various embodiments, a biopsy cap 300 of the present disclosure may be formed from or otherwise include a variety of compressible materials (e.g., silicone, rubbers, etc.) formed as a single unitary structure using, e.g., co-extrusion or co-molding techniques as are known in the art.

Figure 3A:
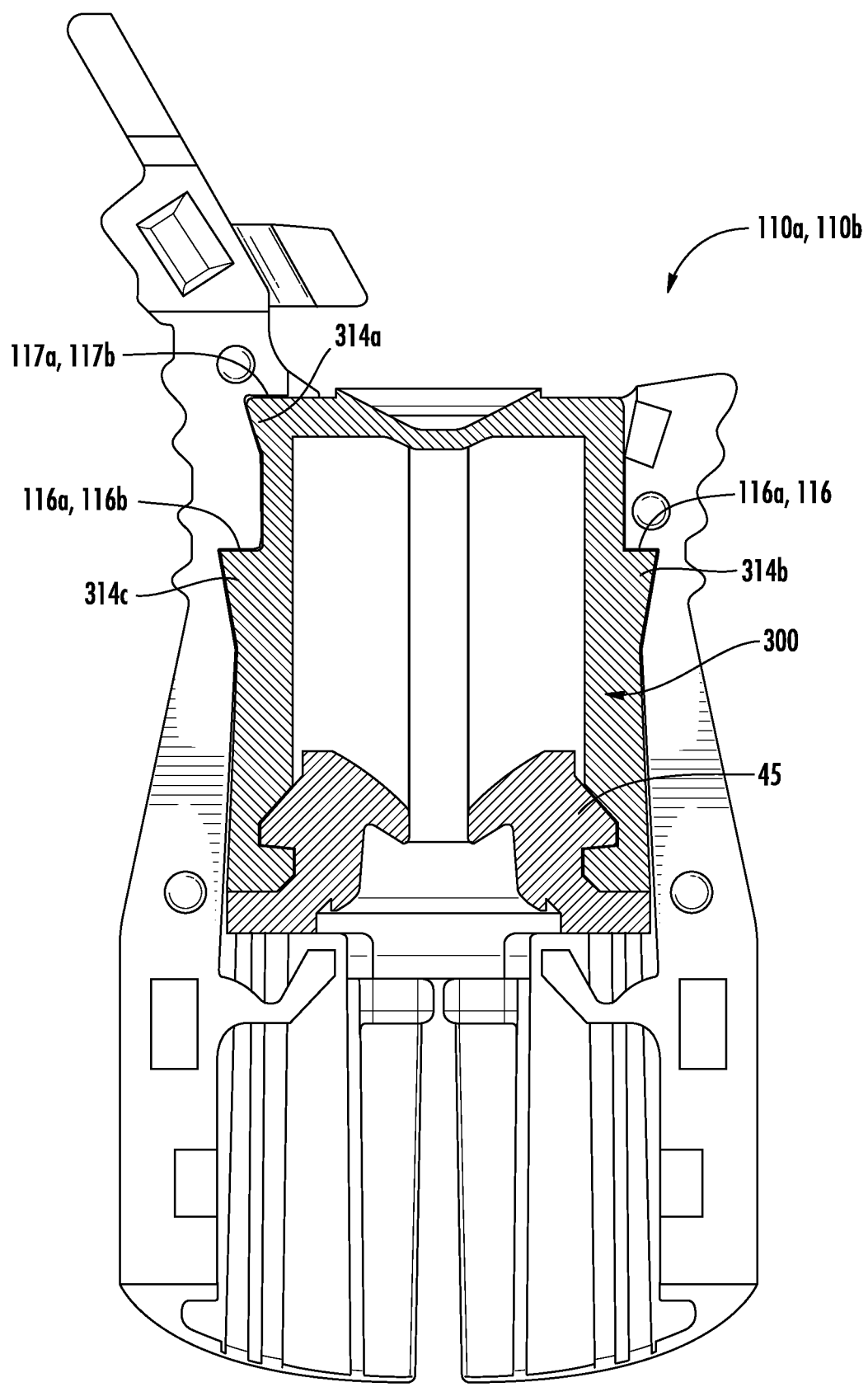
FIGS. 3A-3B provide perspective views of biopsy cap disposed within a biopsy cap housing, according to one embodiment of the present disclosure.
Figure 3B:
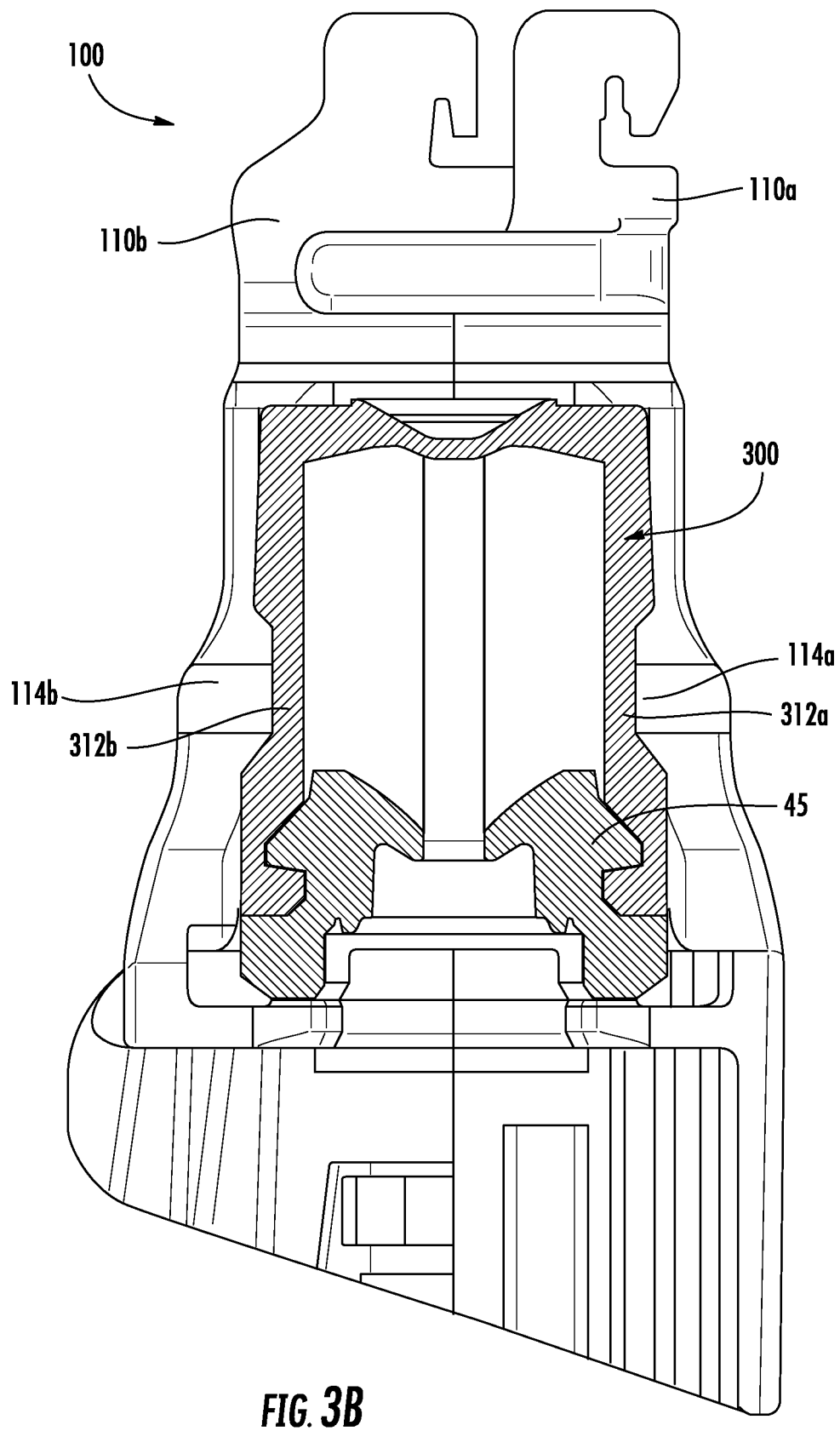

In various embodiments, a variety of advantages may be realized by the biopsy cap housing 20 and/or biopsy cap 300 of the present disclosure. For example, referring to FIG. 3A, in an embodiment the substantially contiguous lip (e.g., formed by respective lips 117a, 117b of the halves 110a, 110b of the housing 100) extending into the upper chamber at or near a proximal end of the biopsy cap housing 100 may frictionally and/or compressingly engage a substantially planar top surface of the first surface feature 314a of the biopsy cap 300. In addition, or alternatively, the contiguous wedges on opposite sides of the first portion (e.g., formed by respective wedges 116a, 116b) may frictionally and/or compressingly engage a substantially planar top surface and/or angled side surface of the respective corresponding second and third surface features 314b, 314c of the biopsy cap 300 and a base 45. Referring to FIG. 3B, in addition or alternatively, the elevated surfaces of the first and second pivot members 114a, 114b may frictionally and/or compressingly engage corresponding recessed portions 312a, 312b formed within an outer wall of a biopsy cap 300.

In various embodiments, the cumulative effect of these frictional and/or compressive forces along various opposing surfaces and sides of the biopsy cap 300 may limit or prevent axial and/or rotational movement of the biopsy cap 300 within the first portion (upper chamber) of the biopsy cap housing 100 and/or prevent fluid flow (e.g., leakage) around an outer surface of the biopsy cap 300, e.g., during device exchange through a lumen 310 of the biopsy cap 300.

In addition, or as an alternative, to the above-described advantages, a variety of additional advantages may be realized by the interlocking projections and receiving elements of the respective first and second center-split halves 110a, 110b. For example, the interlocking pin(s) 118a/pin hole(s) 118b and snap-lock(s) 120a/snap-lock receiver(s) 120b may provide structural support, minimize movement and equally distribute radially outward forces exerted on the biopsy cap housing 100 across and/or between the first and second center-split halves 110a, 110b. For example, radial outward forces exerted on the biopsy cap housing 100 during exchange of a large (e.g., 16-French) medical instrument through the flexible biopsy cap 300 may be distributed substantially equally along a full length of the biopsy cap housing 100 (e.g., between/along mating surfaces 111a, 111b) rather than concentrated within the upper chamber. In addition, radial outward forces applied unequally to one side of the biopsy cap housing 100, e.g., by a guidewire secured to the first and/or second locking hooks 123a, 123b may be redistributed substantially equally along a full length of the biopsy cap housing 100. In addition, or alternatively, the larger surface area of the interlocking peg(s) 119a/sockets 119b (e.g., as compared to the pin(s) 118a/pinhole(s) 118b) at or near the locking member(s) 124a, 124b may provide additional structural support, minimize movement and equally distribute forces at or near the lower portion of the biopsy cap housing 100, e.g., adjacent to the locking member(s) 124a, 124b which reversibly engage the neck 410 of the endoscope biopsy port 400.

In addition, or as an alternative, to any of the above-described advantages, a variety of additional advantages may be realized by the first and second pivot members 114a, 114b of the respective first and second center-split halves 110a, 110b. For example, in addition to providing an elevated surfaces to frictionally and/or compressingly engage corresponding recessed portions 312a, 312b formed within an outer wall of a biopsy cap 300, the first and second pivot members 114a, 114b may include an increased thickness (e.g., as compared to the remaining wall thickness of the first portions 112a, 112b of the first and second center-split halves 110a, 110b) to provide a strengthened or otherwise fortified section of the biopsy cap housing 100 at a pivot point (e.g., high-stress portion) between the upper and lower chambers. For example, a user may inwardly compress the second portions 122a, 122b of the biopsy cap housing 100 such that the first portions 112a, 112b of the first and second center-split halves 110a, 110b move away from each other and the second portions 122a, 122b of the first and second center-split halves 100a, 110b move towards each other to engage the locking members 124a, 124b of the lower chamber with the neck 410 of the endoscope biopsy port 400 (FIG. 4A). Similarly, a user may inwardly compress the first portions 112a, 112b of the biopsy cap housing 100 such that the first portions 112a, 112b of the center-split halves 110a, 110b move toward each other and the second portions 122a, 122b of the first and second center-split halves 110a, 110b move away from each other to disengage the locking members 124a, 124b from the neck 410 of the endoscope biopsy port 400. In various embodiments, the shape, location and/or thickness of the first and second pivot members 114a, 114b may provide increased strength and/or flexibility as compared to a corresponding pivot point of a conventional biopsy cap housing without increasing the overall amount of material at the first and second pivot members 114a, 114b.

As will be understood by those of skill in the art, the substantially equal distribution of forces throughout the biopsy cap housing 100, including radially outward forces due to device exchange or guidewire locking and high-stress forces at the pivot points due to attachment/removal from the biopsy port, may reduce the cumulative effects of wear-and-tear resulting from incremental and persistent movement between the interlocking projections and receiving elements and/or prevent partial or complete disengagement of the lower housing from the neck 410 of the endoscope biopsy port 400.

Figure 4B:
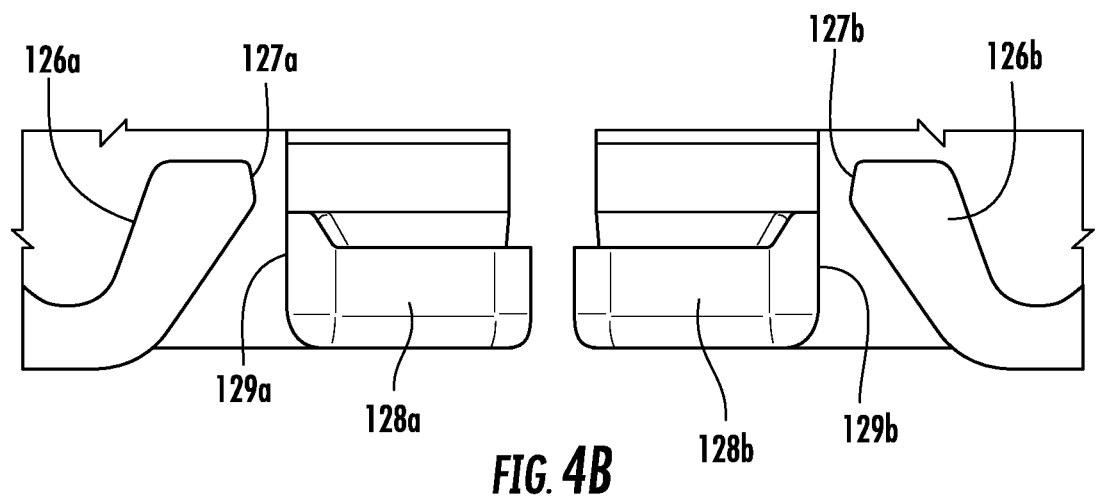
Figure 4C:
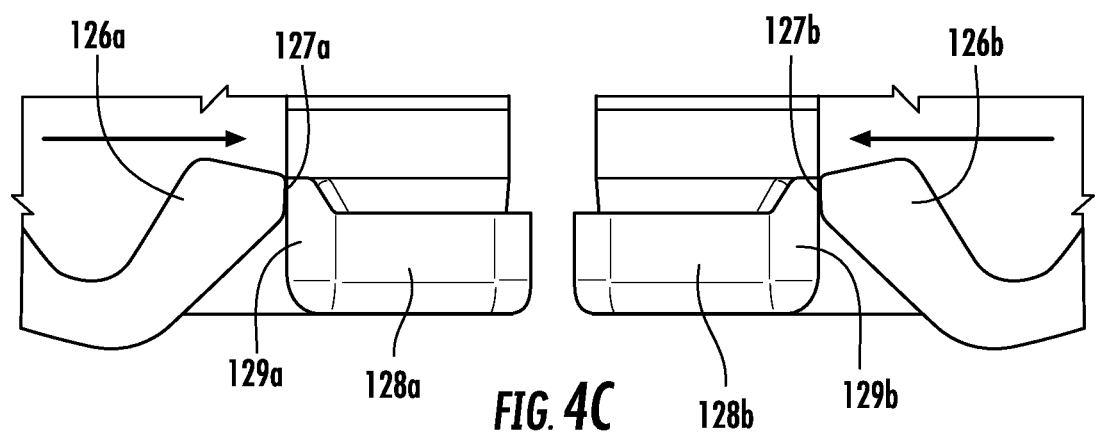

Referring to FIG. 4A, in one embodiment, the locking members 124a, 124b (e.g., V-locks, etc.) may releasably engage the neck 410 of a biopsy port 400 disposed within the lower chamber, e.g., when the second portions 122a, 122b of the biopsy cap housing 100 are inwardly compressed towards each other. Referring to FIG. 4B, with the locking members 124a, 124b releasably engaged with the neck 410 of the biopsy port 400, and end of the locking members 124a, 124b may be separated from a surface 129a, 129b (e.g., enlarged or thickened surface) of a respective platform 128a, 128b by a distance. Referring to FIG. 4C, with the locking members disengaged from the neck 410 of the biopsy port 400, e.g., when the first portions 112a, 112b of the biopsy cap housing 100 are inwardly compressed towards each other, the ends of the locking members 124a, 124b may contact the respective surface 129a, 129b of the platforms 128a, 128b to prevent the locking members 124a, 124b from over-extending to a point of fracture. For example, the surfaces 129a, 129b may prevent the locking members 124a, 124b from extending past the respective the platforms 128a, 128b to a point at which one or both of the locking members 124a, 124b might break or otherwise fracture. By way of non-limiting example, the platform 128a, 128b may be configured or positioned to allow the locking members 124a, 124b to bend or flex approximately 15-degrees and not greater than approximately 25-degrees.

In addition, or as an alternative, to any of the above-described advantages, the ability of the platforms of the stabilizers 128a, 128b to prevent over-extension of the locking members 124a, 124b may further prevent or minimize the cumulative effects of wear-and-tear resulting from incremental and persistent over-extension of the locking members 124a, 124b before or following repeated engagement and disengagement with the neck 410 of the endoscope biopsy port 400.

In various embodiments, the first and second center-split halves 110a, 110b, may be integrally formed from (co-molded, co-extruded, injection molded etc.) a variety of high-quality polymers (e.g., acetyl, etc.) which may provide the requisite yield strain and force modulus to withstand the various radial and load forces exerted on the biopsy cap housing 100 while also maintaining sufficient flexibility to be opened or closed using the force applied by a user's fingers.

The present disclosure is not limited to embodiments in which the one or more projections are located exclusively on a mating surface of the first center-split half and the corresponding one or more receiving elements are located exclusively on a mating surface of the second center-split half. In various embodiments, the one or more projections may be located on a mating surface of the second center-split half and the corresponding one or more receiving elements may be located on a mating surface of the first center-split half. In various additional embodiments, the mating surface of the first center-split half may include both projections and receiving elements configured to receive and/or be received within corresponding receiving elements and projections on the mating surface of the second center-split half.

All of the devices and/or methods disclosed and claimed herein can be made and executed without undue experimentation in light of the present disclosure. While the devices and methods of this disclosure have been described in terms of preferred embodiments, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. A biopsy cap assembly, comprising:
    a biopsy cap housing defining an upper chamber and a lower chamber, the biopsy cap housing comprising:
        a first center-split half comprising:
            a first portion defining a first half of the upper chamber;
            a second portion defining a first half of the lower chamber; and
            a first pivot member integrally formed with the first portion of the first center-split half and including an elevated surface extending into the upper chamber; and
        a second center-split half comprising:
            a first portion defining a second half of the upper chamber;
            a second portion defining a second half of the lower chamber; and
            a second pivot member integrally formed with the first portion of the second center-split half and including an elevated surface extending into the upper chamber;
        wherein mating surfaces of the first and second center-split halves are configured to interlock to define the upper and lower chambers; and
    a biopsy cap disposed within the upper chamber of the biopsy cap housing and including a first recessed portion and a second recessed portion corresponding to and engaged by the first pivot member and the second pivot member, respectively.

2. The biopsy cap assembly of claim 1, wherein:
    a first slit extends through a sidewall of the first and second portions of the first center-split half and is in substantial alignment with the first pivot member; and
    a second slit extends through a sidewall of the first and second portions of the second center-split half and is in substantial alignment with the second pivot member.

3. The biopsy cap assembly claim 1, wherein the elevated surface of the second pivot member extends into the upper chamber substantially opposite the first pivot member.

4. The biopsy cap assembly of claim 3, wherein the first and second pivot members include a thickness greater than a wall thickness of the first and second center-split halves.

5. The biopsy cap assembly of claim 3, wherein the pivot members include an increased thickness to provide a strengthened or otherwise fortified section of the biopsy cap housing.

6. The biopsy cap assembly of claim 1, wherein a surface feature formed on or within the biopsy cap is configured to frictionally and/or compressingly engage with a surface feature formed on or within an inner surface of the first portion of the first and second center-split halves.

7. The biopsy cap assembly of claim 6, wherein the surface feature of the housing includes a pair of lips integrally formed with an inner wall of the first and second center-split halves and extending into the first half of the upper chamber at or near a proximal end of the first portion.

8. The biopsy cap assembly of claim 7, wherein the lips align to form a substantially contiguous lip extending into the upper chamber at or near a proximal end of the housing.

9. The biopsy cap assembly of claim 8, wherein the biopsy cap includes a first surface feature attached to or integrally formed with a proximal end of the biopsy cap and the substantially contiguous lip frictionally and/or compressingly engages with a substantially planar top surface of the first surface feature.

10. The biopsy cap assembly of claim 7, wherein:
the surface feature of the housing includes a pair of wedges formed within the inner wall of the first portion distal to the pair of lips and on opposite sides of the first half of the first portion;
the wedges substantially align to form contiguous wedges on opposite sides of the upper chamber;
the biopsy cap includes second and third surface features attached to or integrally formed with an outer wall of the biopsy cap; and
the contiguous wedges frictionally and/or compressingly engage a substantially planar top surface and/or angled side surface of the respective corresponding second and third surface feature.

11. The biopsy cap assembly of claim 1, wherein an inner surface of the second portions of the first and second center-split halves include one or more locking members extending into the lower chamber.

12. The biopsy cap assembly of claim 11, wherein the inner surface of the second portions of the first and second center-split halves include one or more platforms extending into the lower chamber on opposite sides of the first and second slits and between the one or more locking members.

13. The biopsy cap assembly of claim 12, wherein an end of the one or more locking members and a surface of the one or more platforms are in contact with each other when a force is applied to the first portions of the first and second center-split halves.

14. The biopsy cap assembly of claim 11, wherein the one or more locking members are two locking members, and wherein the two locking members releasably engage a neck of a biopsy port disposed within the lower chamber, when second portions of the housing are inwardly compressed towards each other.

15. The biopsy cap assembly of claim 14, wherein:
the inner surface of the second portions of the first and second center-split halves include one or more platforms extending into the lower chamber between the one or more locking members; and
when the locking members releasably engage the neck of the biopsy port, an end of the locking members is separated from a surface of the respective platform.

16. The biopsy cap assembly of claim 14, wherein:
the inner surface of the second portions of the first and second center-split halves include one or more platforms extending into the lower chamber between the one or more locking members; and
when the locking members are disengaged from the neck of the biopsy port, an end of the locking members contacts a surface of the respective platform.

17. The biopsy cap assembly of claim 11, wherein an end of the locking members includes a pair of substantially perpendicular surfaces configured to engage a substantially 90-degree surface of the neck of the biopsy port.

18. The biopsy cap assembly of claim 1, wherein an inner surface of the first portions of at least one of the first and second center-split halves includes a surface feature configured to engage a corresponding surface feature formed on or within an outer wall of a biopsy cap disposed within the upper chamber.

19. The biopsy cap assembly of claim 18, wherein the surface feature of the at least one of the first and second center-split halves includes a lip extending into a proximal end of the upper chamber, and wherein the surface feature of the biopsy cap includes a wedge extending outward from a top surface of the cap, and wherein the lip is configured to engage the top surface of the wedge.

20. The biopsy cap assembly of claim 18, wherein the surface feature of at least one of the first and second center-split halves includes a wedge formed within the inner surfaces of the first and second portions of the first and second center-split halves, the surface feature of the biopsy cap includes a wedge extending outward from an outer wall of the biopsy cap top, and wherein the wedge of the housing is configured to engage the wedge of the biopsy cap.

* * * * *